United States Patent
Manabe

(10) Patent No.: US 11,241,322 B2
(45) Date of Patent: Feb. 8, 2022

(54) DRUG-ELUTING STENT

(71) Applicant: JIMRO CO., LTD., Takasaki (JP)

(72) Inventor: Matsuya Manabe, Tokyo (JP)

(73) Assignee: JIMRO CO., LTD., Takasaki (JP)

( * ) Notice: Subject to any disclaimer, the term of this patent is extended or adjusted under 35 U.S.C. 154(b) by 654 days.

(21) Appl. No.: 15/522,406

(22) PCT Filed: Oct. 21, 2015

(86) PCT No.: PCT/JP2015/079693
§ 371 (c)(1),
(2) Date: Apr. 27, 2017

(87) PCT Pub. No.: WO2016/067994
PCT Pub. Date: May 6, 2016

(65) Prior Publication Data
US 2017/0319362 A1 Nov. 9, 2017

(30) Foreign Application Priority Data

Oct. 28, 2014 (JP) .............................. JP2014-219159

(51) Int. Cl.
| | |
|---|---|
| *A61F 2/90* | (2013.01) |
| *A61L 31/16* | (2006.01) |
| *A61L 31/10* | (2006.01) |
| *A61F 2/82* | (2013.01) |
| *A61L 31/14* | (2006.01) |
| *A61K 31/4709* | (2006.01) |

(52) U.S. Cl.
CPC .................. *A61F 2/90* (2013.01); *A61F 2/82* (2013.01); *A61K 31/4709* (2013.01); *A61L 31/10* (2013.01); *A61L 31/14* (2013.01); *A61L 31/148* (2013.01); *A61L 31/16* (2013.01); *A61F 2250/0067* (2013.01); *A61L 2300/42* (2013.01); *A61L 2300/434* (2013.01)

(58) Field of Classification Search
None
See application file for complete search history.

(56) References Cited

U.S. PATENT DOCUMENTS

| 5,637,113 A * | 6/1997 | Tartaglia ................... A61F 2/07 604/104 |
|---|---|---|
| 5,756,553 A * | 5/1998 | Iguchi ..................... A61L 27/54 424/425 |

(Continued)

FOREIGN PATENT DOCUMENTS

| CN | 1355005 A | 6/2002 |
|---|---|---|
| CN | 1655738 A | 8/2005 |

(Continued)

OTHER PUBLICATIONS

Communication dated May 18, 2018, from the European Patent Office in counterpart European Application No. 15856064.9.

(Continued)

*Primary Examiner* — Leslie Lopez
(74) *Attorney, Agent, or Firm* — Sughrue Mion, PLLC

(57) ABSTRACT

A drug-eluting stent whose main body is made of a metal or a polymeric material, the surface of which is coated with a mixture including cilostazol and a bioabsorbable polymer, wherein the molecular weight of the bioabsorbable polymer is 40,000 to 600,000.

8 Claims, 6 Drawing Sheets

(56) References Cited

U.S. PATENT DOCUMENTS

| | | | |
|---|---|---|---|
| 6,607,548 B2 * | 8/2003 | Pohjonen | A61L 27/26 606/105 |
| 2003/0219562 A1 * | 11/2003 | Rypacek | A61L 31/10 428/36.91 |
| 2005/0112273 A1 | 5/2005 | Stenzel | |
| 2005/0246009 A1 | 11/2005 | Toner et al. | |
| 2006/0019929 A1 | 1/2006 | Friesen | |
| 2006/0020243 A1 | 1/2006 | Speck et al. | |
| 2006/0161242 A1 | 7/2006 | Lee et al. | |
| 2006/0171982 A1 | 8/2006 | Timm | |
| 2006/0177416 A1 * | 8/2006 | Turnell | A61K 9/5153 424/78.27 |
| 2006/0205727 A1 | 9/2006 | Kaesemeyer | |
| 2006/0212109 A1 * | 9/2006 | Sirhan | A61F 2/91 623/1.16 |
| 2006/0240014 A1 | 10/2006 | Sukhatme | |
| 2007/0098753 A1 | 5/2007 | Falotico et al. | |
| 2008/0124450 A1 | 5/2008 | Pacetti | |
| 2008/0147177 A1 | 6/2008 | Scheuermann et al. | |
| 2010/0198344 A1 | 8/2010 | Omura et al. | |
| 2010/0233229 A1 | 9/2010 | Nakagawa et al. | |
| 2010/0241220 A1 | 9/2010 | McClain et al. | |
| 2010/0280600 A1 * | 11/2010 | Dave | A61L 31/16 623/1.42 |
| 2011/0137407 A1 | 6/2011 | Nguyen et al. | |
| 2012/0213838 A1 | 8/2012 | Egashira et al. | |
| 2013/0304183 A1 | 11/2013 | Sawada et al. | |

FOREIGN PATENT DOCUMENTS

| | | | |
|---|---|---|---|
| CN | 1669595 A | 9/2005 | |
| CN | 1669596 A | 9/2005 | |
| CN | 1669597 A | 9/2005 | |
| EP | 1 516 597 A1 | 3/2005 | |
| EP | 3 064 232 A1 | 9/2016 | |
| JP | 2001-190687 A | 7/2001 | |
| JP | 2003-290360 A | 10/2003 | |
| JP | 2004-523275 A | 8/2004 | |
| JP | 2005-508671 A | 4/2005 | |
| JP | 2005-531391 A | 10/2005 | |
| JP | 2005-538812 A | 12/2005 | |
| JP | 2006-198390 A | 8/2006 | |
| JP | 2006-526652 A | 11/2006 | |
| JP | 2007-215620 A | 8/2007 | |
| JP | 2007-528275 A | 10/2007 | |
| JP | 2007-529285 A | 10/2007 | |
| JP | 2008-505126 A | 2/2008 | |
| JP | 2008-517669 A | 5/2008 | |
| JP | 2008-528244 A | 7/2008 | |
| JP | 2008-533044 A | 8/2008 | |
| JP | 2009-511195 A | 3/2009 | |
| JP | 2009-511205 A | 3/2009 | |
| JP | 2010-506837 A | 3/2010 | |
| JP | 2010-506849 A | 3/2010 | |
| JP | 2010-508975 A | 3/2010 | |
| JP | 2010-509998 A | 4/2010 | |
| JP | 4473390 B2 | 6/2010 | |
| JP | 2011-172927 A | 9/2011 | |
| JP | 2013-126558 A | 6/2013 | |
| JP | 2013-236940 A | 11/2013 | |
| JP | 2007-117742 A | 5/2017 | |
| WO | 02/056790 A2 | 7/2002 | |
| WO | 2003/009779 A2 | 2/2003 | |
| WO | 03/099169 A1 | 12/2003 | |
| WO | 2004/010900 A1 | 2/2004 | |
| WO | 2005/086831 A2 | 9/2005 | |
| WO | 2007/047416 A2 | 4/2007 | |
| WO | 2007/047473 A2 | 4/2007 | |
| WO | 2008/045961 A2 | 4/2008 | |
| WO | 2008/063319 A2 | 5/2008 | |
| WO | 2010/111238 A2 | 9/2010 | |
| WO | 2010/127584 A1 | 11/2010 | |
| WO | 2011/024831 A1 | 3/2011 | |
| WO | 2012/111241 A1 | 8/2012 | |

OTHER PUBLICATIONS

Communication dated Sep. 21, 2018, from the European Patent Office in Counterpart application No. 15856064.9.

Communication dated Dec. 4, 2018, from European Patent Office in counterpart application No. 15856064.9.

International Preliminary Report on Patentability dated Feb. 14, 2017, in counterpart application No. PCT/JP2015/079693.

International Search Report for PCT/JP2015/079693, dated Dec. 8, 2015.

* cited by examiner

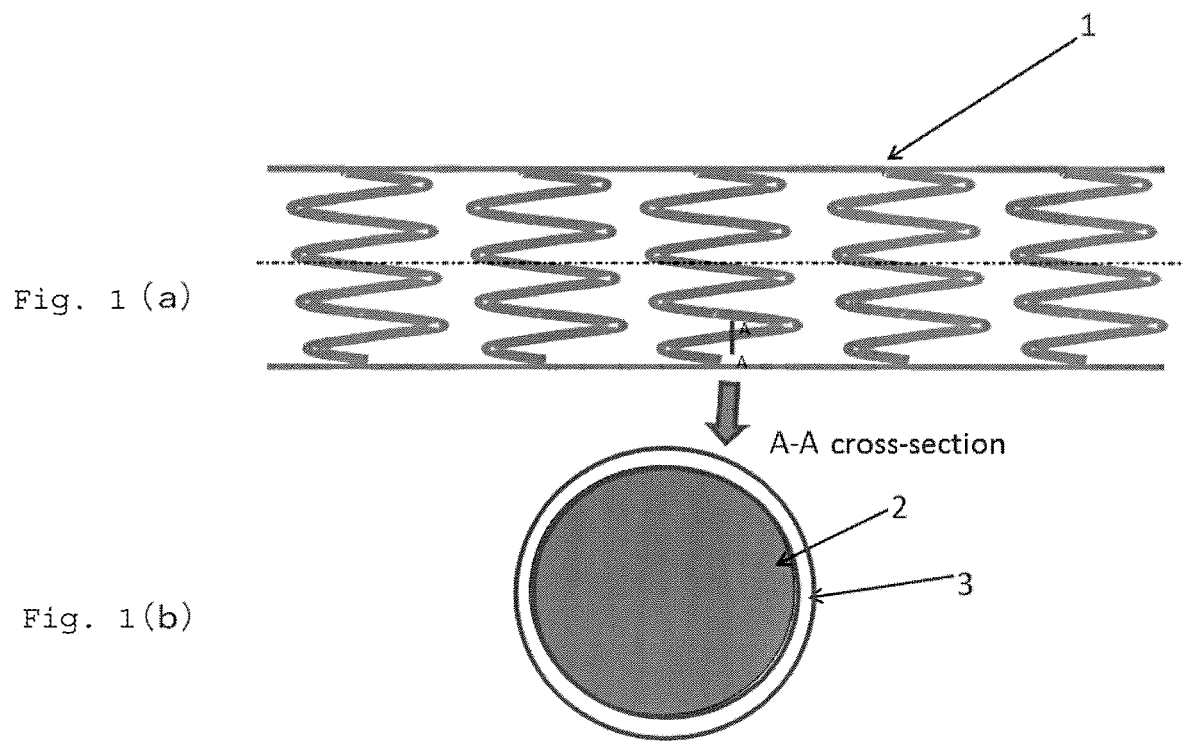
Fig. 1(a)
Fig. 1(b)
A-A cross-section
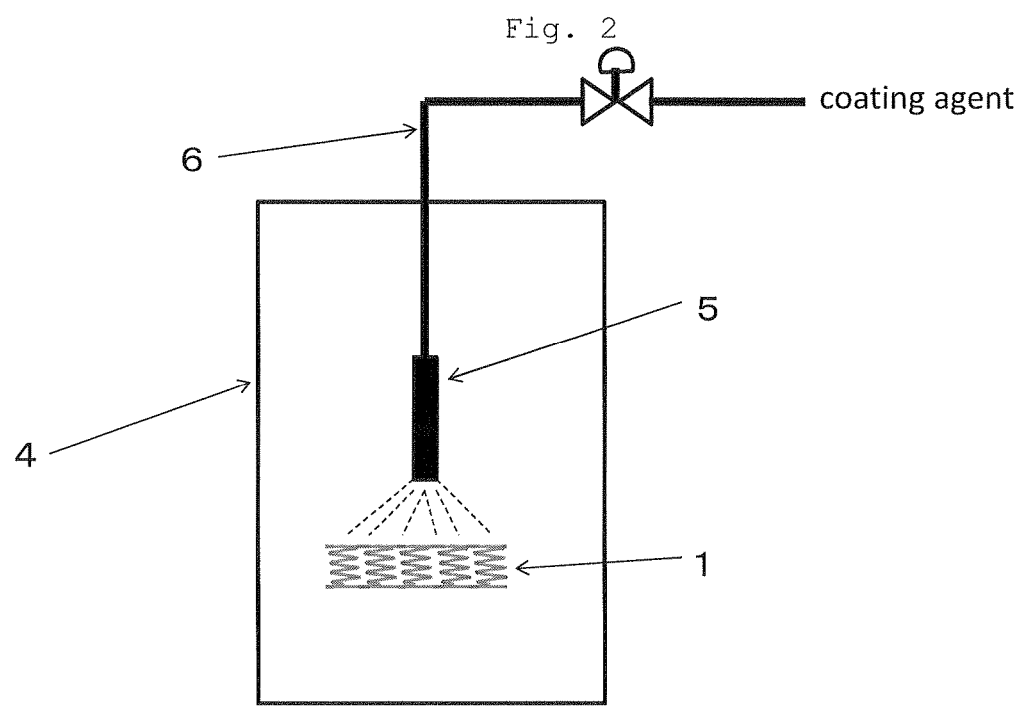
Fig. 2

DRUG-ELUTING STENT

CROSS REFERENCE TO RELATED APPLICATIONS

This is a National Stage of Application No. PCT/JP2015/079693 filed Oct. 21, 2015, claiming priority based on Japanese Patent Application No. 2014-219159 filed Oct. 28, 2014, the contents of all of which are incorporated herein by reference in their entirety.

TECHNICAL FIELD

The present invention may relate to a stent coated with cilostazol and a process for preparing it.

BACKGROUND ART

The current advancement of medicine brings about a remarkable development of the treatment/prevention of various diseases such as infection disease, but patients of arteriosclerotic disease or the like which is caused by bad lifestyle tend to increase. In particular, patients of arteriosclerotic disease such as myocardial infarction, angina, stroke, and peripheral vascular disease are increasing more and more in Japan, in connection with the westernization of lifestyle and the aging. As a method for surely treating such arteriosclerotic disease, percutaneous transluminal angioplasty (hereinafter, referred to as "PTA") is generally used, which is an angioplasty to surgically expand the stenosis or occluded part in blood vessel, for example, percutaneous transluminal coronary angioplasty in coronary artery which is typical. The PTA which is operated for the stenotic or occlusive area in coronary artery is specifically referred to as Percutaneous Transluminal Coronary Angioplasty, (abbreviated as "PTCA").

The PTCA is a technique for recovering the blood flow, in which a balloon catheter (a tube having a balloon at its tip) or a stent is inserted from an arm or femoral artery, it is placed at a stenosis in the coronary artery, then the balloon attached at the tip is blown up to expand the stenotic blood vessel. This technique can expand an intravascular lumen in a lesion site to increase the blood flow in the intravascular lumen. The PTCA is used for the treatment of arteriosclerotic disease as well as shunt stenosis which arises at an arm of a hemodialysis patient.

In general, the PTCA-treated blood vessel is damaged such as detachment of endothelial cell and injury of elastic lamina, and the vascular intima grows because of the healing reaction in the vascular wall, thereby patients whose stenosis lesion site is opened by PTCA can suffer from restenosis at a rate of about 30 to 40%.

In more detail, the main cause of restenosis in human beings is thought to be the inflammatory process (adhesion/invasion of a monocyte) arising 1 to 3 days after the PTCA, and the forming process of intimal thickening (smooth muscle cell) whose growth is the most about 45 days after the PTCA. Once the restenosis comes up, it is necessary to do the PTCA again. Accordingly, the establishment of the method for the prevention and treatment has been desired.

Then, it has been suggested to try reducing the rate of restenosis by releasing a drug topically for a long time at a site for placement in a lumen, using a drug-dissolution type of a medical device (stent) for placement into a lumen wherein an anticancer agent or an immunosuppressive agent, as well as an anti-inflammatory agent or an inhibitor of smooth-muscle cell proliferation is supported on the surface of stent or balloon catheter which is made of metal or polymer material.

The drugs applied on a drug-eluting stent are generally limus-type drugs such as an anticancer agent and an immunosuppressive agent. These drugs have a potent effect to suppress the growth of vascular smooth muscle cell, so-called "intimal thickening" which is a main cause of restenosis, thanks to their potent cytotoxicity. On the contrary, these drugs can also strongly inhibit the regeneration of vascular endothelial cell, which can induce delayed in-stent thrombosis that is a big clinical problem. The incidence rate of delayed in-stent thrombosis is small, less than 1%, but, once the patient given with the stent suffers from the thrombosis, the patient can have a bad prognosis, i.e., can suffer a serious problem such as cardiac death.

In order to solve the problem, it has been actively studied now to suppress the inhibitory of the vascular endothelial cell regeneration, for example, by reducing the amount of the above-mentioned limus-type drugs applied on a stent. However, it seems that the problem cannot be completely solved when limus-type drugs are used.

It has been tried to use a drug such as probucol and cilostazol other than limus-type drugs, but, there has not been any practical drug eluting stents other than a stent of limus-type drugs yet.

Patent Reference 1 suggests a drug-eluting stent (hereinafter, abbreviated as "DES") wherein the body of a stent is coated with a biocompatible nanoparticle including a bioactive substance for the treatment, and a process thereof, which discloses a spherical crystallization technique as a process of a biocompatible nanoparticle.

However, a poorly water-soluble drug which is hardly dissolved in water such as probucol and cilostazol which have anti-thrombus activity is hard to be included in a biocompatible nanoparticle by spherical crystallization technique. Actually, when making probucol included in a particle by said spherical crystallization technique, the content of probucol in a PLGA nanoparticle was only about 0.5%, which indicates that little drug was included. Thus, according to the method of Patent Reference 1, it was impossible to prepare a medical device for placement into a lumen wherein the surface is coated with a sufficient amount of a poorly water-soluble drug.

Patent Reference 2 discloses a method of attaching a drug on a carrier by dipping a stent or a catheter which is a carrier to a solution of a drug which is water-insoluble and drying the carrier. In the method disclosed in Patent Reference 2, however, the attached amount was limited, accordingly it was difficult to attach a sufficient amount of a drug on a carrier. In addition, the attached drug was released in a short time, thereby it was also difficult to control the releasing time.

Patent Reference 3 discloses a drug-releasing control type of multilayered stent whose surface is coated with a drug ingredient and a biocompatible polymer as a second coating layer, wherein probucol is listed as one of the exemplified active ingredients. Patent Reference 4 discloses a medical device coated with a biocompatible substance comprising a medicinal ingredient, and Patent Reference 5 discloses a drug delivery system that uses a balloon and an implant prosthesis (stent) which are at least partially coated with a coating agent comprising a drug and a carrier. Further, both of Patent References 4 and 5 disclose probucol as a drug.

However, the methods disclosed in Patent References 3 to 5 had a problem that it takes excessive time to elute a drug and then it is difficult to obtain an enough efficacy of a drug, because a drug ingredient is released in tandem with the decomposition of the biocompatible polymer layer. These methods need to use a solvent which can dissolve both of a drug ingredient and a biocompatible polymer in preparing a liquid coating agent of the drug ingredient and the biocompatible polymer. However, it was restrictive to find such solvent from the viewpoint of the combination of a biocompatible polymer and a drug. Consequently, the methods had a problem of lacking versatility as a coating technique.

In addition, using cilostazol which is another poorly water-soluble drug and has platelet aggregation inhibition action and so on, the same application of the drug to a medical device has been tried (Patent References 3, 6 to 20). For example, Patent Reference 20 discloses a trial that a biocompatible particle is transformed to a nanoparticle thereof, and then a stent is coated with the nanoparticle and cilostazol particle by charge-based method, but the process to prepare it is very complicated. The other methods disclosed in prior art also have the same problem in the trials.

PRIOR ART

Patent Reference

Patent Reference 1: JP 2007-215620 A
Patent Reference 2: JP 2005-538812 T
Patent Reference 3: JP 2006-198390 A
Patent Reference 4: JP 2007-528275 T
Patent Reference 5: JP 2007-529285 T
Patent Reference 6: JP 2007-117742 A
Patent Reference 7: JP 2003-2900360 A
Patent Reference 8: JP 2001-190687 A
Patent Reference 9: JP 4473390 B
Patent Reference 10: JP 2010-506837 T
Patent Reference 11: JP 2010-506849 T
Patent Reference 12: JP 2009-511195 T
Patent Reference 13: JP 2009-511205 T
Patent Reference 14: JP 2008-533044 T
Patent Reference 15: JP 2008-505126 T
Patent Reference 16: JP 2006-526652 T
Patent Reference 17: JP 2005-531391 T
Patent Reference 18: JP 2005-508671 T
Patent Reference 19: JP 2004-523275 T
Patent Reference 20: WO 2011/024831

SUMMARY OF INVENTION

Problems to Be Solved By the Invention

Considering the above problem, the main purpose of the present invention is to provide a drug-eluting stent having both properties (1) suppressing intimal thickening and (2) suppressing the inhibitory of vascular endothelial cell regeneration, in which cilostazol having no cytotoxicity is used as a drug though it does not seem so easy to prepare such stent because cilostazol has poor water-solubility. In detail, the purpose will be achieved by providing a drug-eluting stent which is stably coated with a coating agent comprising cilostazol and a process to prepare the stent.

Means to Solve the Problems

The present inventors have extensively studied in order to solve the above-mentioned problem, and have found that a cilostazol-eluting stent having a suitable coating strength to stably hold cilostazol and a suitable dissolution rate can be prepared by coating a stent with cilostazol along with a bioabsorbable polymer having a certain range of molecular weight, particularly which can be a superior drug-eluting stent to other ones in respect of suppressing intimal thickening because the eluting rate thereof is idealized. Based upon the new findings, the present invention has been completed.

It is expected that the cilostazol-eluting stent cannot cause the inhibitory of vascular endothelial cell regeneration which is caused by limus-type drugs, and can suppress intimal thickening.

The present invention may provide a stent shown in the following Terms 1 to 14, and a process thereof.

(Term 1) A drug-eluting stent having a main body made of a metal or a polymeric material, the surface of which is coated with a mixture comprising cilostazol and a bioabsorbable polymer, wherein the molecular weight of the bioabsorbable polymer is 40,000 to 600,000.

(Term 2) The drug-eluting stent of Term 1 wherein the bioabsorbable polymer comprises (a) a polymer comprising DL lactide and glycolide in a weight ratio of 7:3-9:1, whose molecular weight is 40,000-400,000, (b) a polymer comprising DL lactide whose molecular weight is 50,000-100,000, (c) a polymer comprising L lactide and DL lactide in a weight ratio of 6:4-8:2, whose molecular weight is 300,000-600,000, (d) a polymer comprising L lactide whose molecular weight is 50,000-150,000, or (e) a polymer comprising L lactide and caprolactone in a weight ratio of 6:4-8:2, whose molecular weight is 150,000-400,000.

(Term 3) The drug-eluting stent of Term 1 or 2 wherein the weight ratio of cilostazol and the bioabsorbable polymer is 4:6-7:3.

(Term 4) The drug-eluting stent of Term 3 wherein the weight ratio of cilostazol and the bioabsorbable polymer is 4:6-6:4.

(Term 5) The drug-eluting stent of any one of Terms 1 to 4, whose main body is made of cobalt-chromium alloy as a main ingredient.

(Term 6) The drug-eluting stent of any one of Terms 1 to 5, wherein the coating of the stent body is done by ultrasonic spraying.

(Term 7) The drug-eluting stent of any one of Terms 1 to 6, wherein the weight of cilostazol applied on one stent is more than 400 μg and less than 700 μg.

(Term 8) The drug-eluting stent of Term 7, wherein the weight of cilostazol applied on one stent is more than 500 μg and less than 600 μg.

(Term 9) A process for preparing a drug-eluting stent by coating the surface of the stent with a mixture comprising cilostazol and a bioabsorbable polymer through ultrasonic spraying, wherein the main body of the stent is made of a metal or a polymeric material, and the molecular weight of the bioabsorbable polymer is 40,000 to 600,000.

(Term 10) The process of Term 9, wherein the bioabsorbable polymer comprises (a) a polymer comprising DL lactide and glycolide in a weight ratio of 7:3-9:1, whose molecular weight is 40,000-400,000, (b) a polymer comprising DL lactide whose molecular weight is 50,000-100,000, (c) a polymer comprising L lactide and DL lactide in a weight ratio of 6:4-8:2, whose molecular weight is 300,000-600,000, (d) a polymer comprising L lactide whose molecular weight is 50,000-150,000, or (e) a polymer comprising L lactide and caprolactone in a weight ratio of 6:4-8:2, whose molecular weight is 150,000-400,000.

(Term 11) The process of Term 9 or 10 wherein the weight ratio of cilostazol and the bioabsorbable polymer is 4:6-7:3.

(Term 12) The process of any one of Terms 9 to 11, wherein the weight of cilostazol applied on one stent is more than 400 μg and less than 700 μg.

Effect of the Invention

The drug-eluting stent of the present invention is stably coated with a coating agent comprising cilostazol, has a high coating strength, and especially has a suitable dissolution rate. From the effects, the stent can make the drug eluted at the time of inflammatory process after the stent is indwelled and at the time that restenosis happens in the intimal thickening process, and then the drug can act on intravascular cells, effectively suppress intimal thickening, and drastically improve restenosis which happens in a high rate after the stent is indwelled.

In addition, the drug used herein is cilostazol which has no cytotoxicity, thus the present stent can suppress intimal thickening without inhibiting the vascular endothelial cell regeneration which is caused by limus-type drugs.

BRIEF DESCRIPTION OF DRAWINGS

FIG. 1(a) shows a whole image of a stent, and FIG. 1(b) shows a cross-section view along the line A-A of FIG. 1(a).

FIG. 2 shows an overview of coating a stent by means of a ultrasonic spray machine.

DESCRIPTION OF EMBODIMENTS

Figure 3:
FIG. 3 shows a faulty example of coating in Example 2 (web-like adduct).

It is known that cilostazol used herein whose chemical name is 6-[4-(1-cyclohexyl-1H-tetrazol-5-yl)butoxy]-3,4-dihydrocarbostyril has platelet aggregation inhibition action, phosphodiesterase (PDE) inhibition action, antiulcer, hypotensive action and antiphlogistic action, and is useful as an antithrombotic agent, a drug for improving cerebral circulation, an antiinflammatory agent, an antiulcer drug, an antihypertensive drug, an antiasthmatic drug, a phosphodiesterase inhibitor, etc. Cilostazol also encompasses its pharmaceutically acceptable salt.

The bioabsorbable polymer used herein includes, for example, a polylactide comprising lactide and/or glycolide, whose molecular weight is 40,000 to 600,000. Specifically, the bioabsorbable polymer includes a polymer comprising DL lactide, L lactide, glycolide, caprolactone, etc., in more detail, (a) a polymer comprising DL lactide and glycolide in a weight ratio of 7:3-9:1, whose molecular weight is 40,000-400,000, (b) a polymer comprising DL lactide whose molecular weight is 50,000-100,000, (c) a polymer comprising L lactide and DL lactide in a weight ratio of 6:4-8:2, whose molecular weight is 300,000-600,000, (d) a polymer comprising L lactide whose molecular weight is 50,000-150,000, and (e) a polymer comprising L lactide and caprolactone in a weight ratio of 6:4-8:2, whose molecular weight is 150,000-400,000. Preferably, the bioabsorbable polymer includes the bioabsorbable polymers listed in Table 1 in the Example Section below, or a mixture thereof, more preferably RG858S, RG755S, LR704S, 755/703, or a mixture thereof.

Coating agent 3 comprises a mixture of cilostazol as a medicament and the bioabsorbable polymer mentioned above. The bioabsorbable polymer needs to prevent the coating layer comprising cilostazol from removing because cilostazol is poorly water-soluble, and also needs to maintain a high coating strength.

The mixture ratio by weight of cilostazol and polylactide is preferably 4:6-7:3. When the mixture ratio is within the range, it is expected to gain a good effect to suppress intimal thickening. And, when the mixture ratio is in 4:6-6:4, the coating strength can be further increased.

The stent used herein is a normal stent made of a metal or a polymeric material. In case of a metal stent, the metal includes a suitable alloy of nickel, cobalt, chrome, titanium and/or stainless steel, preferably cobalt-chromium alloy as a main ingredient.

The method for coating a stent with a mixture of cilostazol and bioabsorbable polymer in the present invention includes a conventional simplified spray method, a dipping method, an electrodeposition, a ultrasonic spray method, and the like, preferably a ultrasonic spray method from the viewpoint of the coating strength.

Hereinafter, the embodiments of the present invention are illustrated showing the attached figures. The present inventors have extensively studied in order to solve the problem on conventional drug-eluting stents, and have found that it is possible to prepare a drug-eluting stent which can stably hold cilostazol on the stent and strongly suppress intimal thickening, by coating a metal stent or a polymeric material stent with cilostazol and the polymer mentioned below.

FIG. 1 (a) is a view showing a drug-eluting stent of the present invention. FIG. 1 (b) is a cross-section view of FIG. 1 (a) along the line A-A. Stent 1 has a cylindrical lumen structure having a longer direction axis whose periphery has a net-like pattern, which can be expanded outward. A stent is inserted into a body in an un-expanded state, and then expanded at a treating-target site in a blood vessel to be indwelled in a blood vessel. The expansion may be achieved in a blood vessel with a balloon catheter. FIGS. 1(a) and 1(b) show a net-like pattern as a view, but the present invention can include other net-like patterns.

As shown in FIG. 1 (b), stent 1 of the present invention is coated on base member 2 with coating agent 3. Base member 2 can be prepared in an arbitrary method. For example, it can be prepared from a midair stainless steel tube or a formed stainless steel tube by laser, electric discharge milling, chemical etching, or other methods. Base member 2 can be made of a suitable alloy of nickel, cobalt, chrome, titanium and/or stainless steel.

FIG. 2 is a view showing ultrasonic spray coating machine 4 which applies coating agent 3 on base member 2. Before the coating step, the surface of base member 2 is plasma-treated with a plasma machine which is not shown in FIG. 2. After the plasma treatment, base member 2 is attached to a mandrel, which is fixed in ultrasonic spray coating machine 4. In ultrasonic spray coating machine 4, a liquid coating agent is sent through pipe 6 with a syringe pump, and then atomized and sprayed with ultrasonic spray nozzle 5. While spraying, base member 2 is rotated and linearly moved under ultrasonic spray nozzle 5 to pile up coating agent 3 on base member 2. Subsequently, base member 2 is rotated and linearly moved under nitrogen stream, and further dried in vacuo in a desiccator to prepare stent 1.

The liquid coating agent used herein is a solution of cilostazol and the polymer in a solvent. The solvent used herein includes a volatile solvent having a low boiling point, which can be easily removed after the coating. The volatile solvent includes, for example, methanol, ethanol, trifluoroethanol, hexafluoroisopropanol, isoamyl alcohol, methyl acetate, ethyl acetate, acetone, methyl ethyl ketone, methylene chloride, chloroform, dichloroethane, and a mixture of the two or more solvents.

EXAMPLE

Each polymer listed in the following Table 1 was used in each example below.

TABLE 1

|  | molecular weight | Composition<br>DL: DL lactide<br>G: glycolide<br>L: L lactide<br>C: caprolactone |
|---|---|---|
| (a) | ≈65,000 | DL:G = 45:55-55:45 |
| (b) | ≈32,000 | DL:G = 45:55-55:45 |
| (c) | ≈13,000 | DL:G = 48:52-52:48 |
| (d) | ≈5,900 | DL:G = 45:55-55:45 |
| (e) | ≈63,000 | DL:G = 73:27-77:23 |
| (f) | ≈12,000 | DL:G = 73:27-77:23 |
| (g) | ≈11,000 | DL:G = 73:27-77:23 |
| (h) | ≈77,000 | DL = 100 |
| (i) | ≈28,000 | DL = 100 |
| (j) | ≈220,000 | DL:G = 83:17-87:13 |
| (k) | ≥1,000,000 | L:G = 82:18-88:12 |
| (l) | ≈115,000 | DL = 100 |
| (m) | ≈257,000 | L:C = 67:33-73:23 |
| (n) | ≥1,300,000 | L:DL = 67:37-73:27 |
| (o) | ≥630,000 | L:DL = 67:37-73:27 |
| (p) | ≥350,000 | L:DL = 67:37-73:27 |
| (q) | ≈102,000 | L = 100 |

Example 1

A cobalt-chromium alloy as base member 2 was coated with a mixture of cilostazol and a polymer that was one of the above-listed (e), (j) and (p), wherein the mixing ratio of cilostazol and the polymer was varied as shown in Table 2, through ultrasonic spraying, and each coating strength was evaluated. The results are shown in Table 2. In the table, the symbol "0" indicates that the strength is very high, the symbol "Δ" indicate that the strength is high, and the symbol "x" indicates that the strength is low.

The results indicate that when the mixture ratio of cilostazol and the polymer (D/P ratio) is 6:4 or less, i.e., the amount of cilostazol is less than this ratio, the strength is high, and in particular, when the ratio is 5:5, the strength is enough high. However, when the D/P ratio is less than 4:6, it is assumed that the drug effect of cilostazol used in a drug-eluting stent can decrease. Thus, the D/P ratio is preferably 4:6 or more.

TABLE 2

| D/P ratio | polymer | | | mixed polymer | | | |
|---|---|---|---|---|---|---|---|
|  | (e) | (j) | (P) | (e):(p) | strength | (j):(p) | strength |
| 7/3 | x | Δ | Δ | 2:1 | x | 2:1 | x |
|  |  |  |  | 1.5:1.5 | x | 1.5:1.5 | x |
|  |  |  |  | 1:2 | x | 1:2 | x |
| 6/4 | Δ | Δ | Δ | 3:1 | Δ | 3:1 | Δ |
|  |  |  |  | 2:2 | Δ | 2:2 | Δ |
|  |  |  |  | 1:3 | Δ | 1:3 | Δ |
| 5/5 | o | o | o | 1:4 | o | 1:4 | Δ |
|  |  |  |  | 2.5:2.5 | Δ | 2.5:2.5 | Δ |
|  |  |  |  | 4:1 | Δ | 4:1 | o |

Example 2

A cobalt-chromium alloy as base member 2 was coated with a coating agent prepared by mixing cilostazol and one of the 17 polymers (a) to (q) listed in Table 1, through ultrasonic spraying. The mixing ratio of cilostazol and each polymer was 5:5.

Figure 4:
FIG. 4 shows a faulty example of coating in Example 2 (uneven coating).
Figure 5:
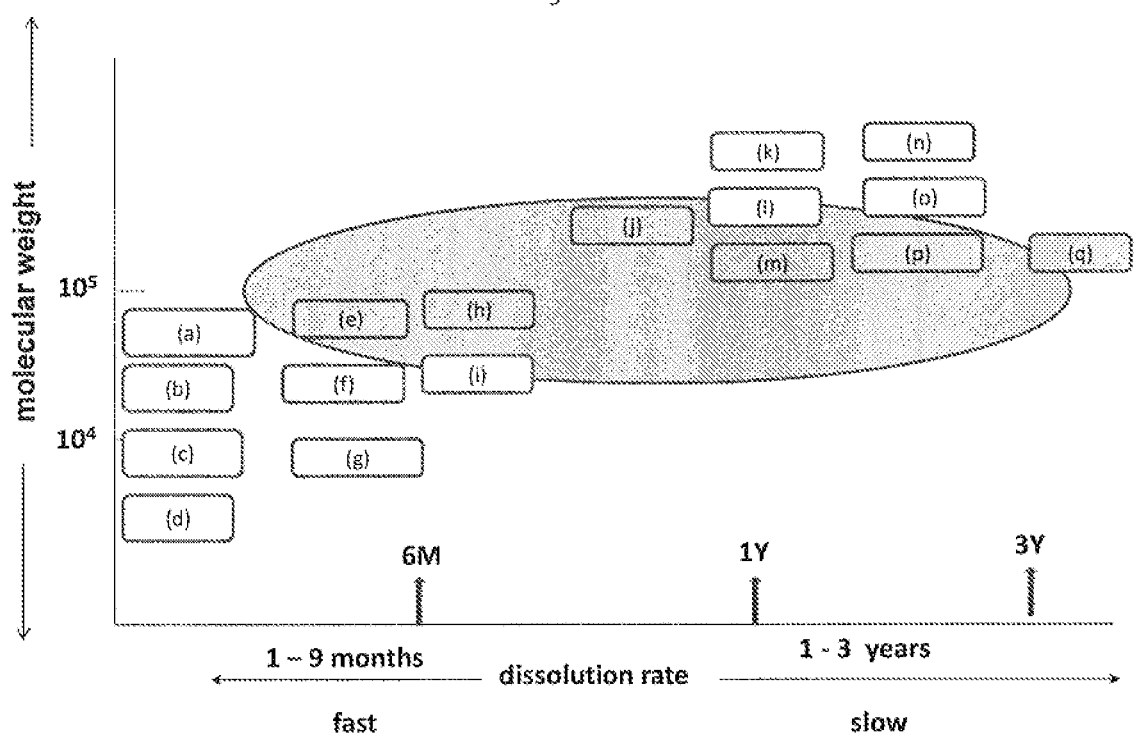
FIG. 5 shows the result of Example 2.

The outer appearance of each prepared stent was observed about the coating work. In the external observation, coated stents having no web-like adduct shown in FIG. 3 or no uneven coating shown in FIG. 4 in the coated stents, and whose surface is not like orange peel but flat and smooth, were evaluated as "good". The results are shown in FIG. 5. In FIG. 5, the axis of ordinate denotes the molecular weight of each polymer mixed with cilostazol and the axis of abscissas denotes the dissolution rate of the coating agent. The (a) to (q) indicated in FIG. 5 which are the 17 polymers listed in Table 1 show the relation of the two factors by their positions.

As the evaluation of the coating performance, the polymers in the area circled with a ellipse in FIG. 5 exhibited a tendency of good coatings. FIG. 5 indicates that the coating performance cannot be greatly affected by the dissolution rate, but it tends to be affected by the molecular weight of the polymers. The polymer to be used in a coating agent comprising cilostazol is preferably a polymer having a molecular weight of 40,000-600,000. In particular, it was observed that polymers (e), (h), (j), (m), (p), and (q) in a coating agent can bring in a good coating performance.

Example 3

Stents were prepared with the above polymers (e), (h), (j), (m), (p), and (q) in a similar manner to Example 2. As explained below, each prepared stent was placed in the iliac blood vessel of rabbits, and the effect of each stent to suppress intimal thickening was evaluated.

First, the neck of a rabbit is incised, and the right carotid artery is exteriorized, to which an introducer is attached. A guidewire for balloon catheter is inserted from the introducer and moved under X-ray fluoroscopy to the distal portion of the iliac artery to be treated. And then, an angiographic catheter is inserted along the guidewire, and the angiography is performed at the disposing site of the iliac artery. After the angiography at the disposing site, a balloon catheter with the test stent is inserted to the disposing site along the guidewire for balloon catheter under X-ray fluoroscopy. The test stent (wherein the stent diameter is 2.75 mm when the standard diameter dilating pressure is 9 atm) is placed at the disposing site of the iliac artery (the blood vessel diameter is assumed to be 2.5 mm) and then the balloon is expanded with an indeflator holding the pressure of 14 atm (over-expanded, assumed stent diameter: 3.0 mm, 20% over-expanded) for 20 seconds one time. After confirming that the stent is expanded, the balloon is deflated, the indeflator is removed out, and the balloon catheter is pulled out along the guidewire for balloon catheter. The same procedure is performed at the right and left of the iliac artery.

Next, the angiographic catheter is moved close to the disposing site along the guidewire for balloon catheter, and there the angiography is performed with a diluted contrast agent. The same procedure is performed at the right and left of the iliac artery, and then the angiographic catheter is pulled out. Finally, the blood vessel at the sheath insertion site is ligated, and the skin and muscle layer are sewn up. In this way, the stent can be placed in the iliac blood vessel of rabbits.

The intimal thickening was tested by observing the stent-placed site with the angiographic pictures recorded on DVD before the placement, shortly after the placement of the stent (reference diameter), and before the autopsy (28 days after the placement). And the intimal thickening was evaluated based on the difference between the reference diameter shortly after the placement of the stent and the narrowest blood vessel diameter before the autopsy.

Figure 6:
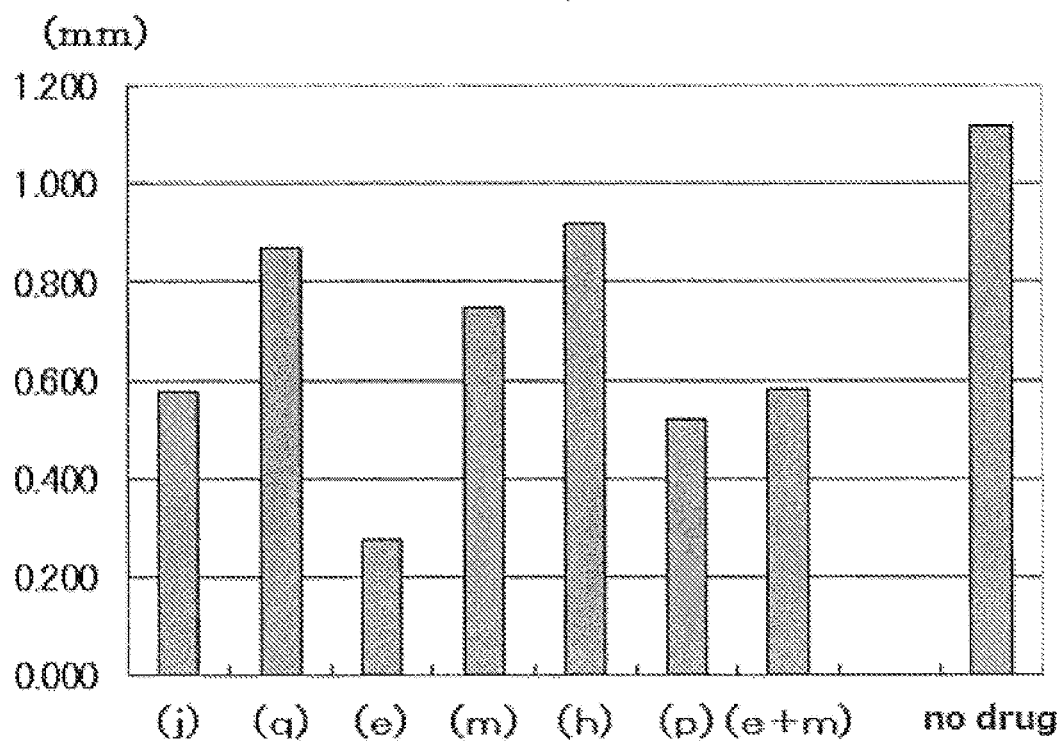
FIG. 6 shows the result of Example 3.

FIG. 6 shows the results. The term "no drug" in FIG. 6 means that the stent is not coated with cilostazol. The other results are based on the stents which are coated with each coating agent comprising mixtures the above polymers and cilostazol in a ratio of 5:5.

The axis of ordinate in FIG. 6 denotes the intimal thickening, i.e., when the length is smaller, it means that the effect of suppressing intimal thickening is higher.

The result of (j) which includes cilostazol shows that the intimal thickening is greatly suppressed. Similarly, the results of (e) and (p) also showed that the coating with cilostazol can suppress intimal thickening. In addition, the observation of the endothelial cells at the stent-placing site showed that the endothelial cells could be well regenerated, and thus, the present stent coated with cilostazol was able to achieve the both effects of (1) suppressing intimal thickening and (2) suppressing the inhibitory of the vascular endothelial cell regeneration, which have not been achieved with limus-type drugs.

Example 4

Figure 7:
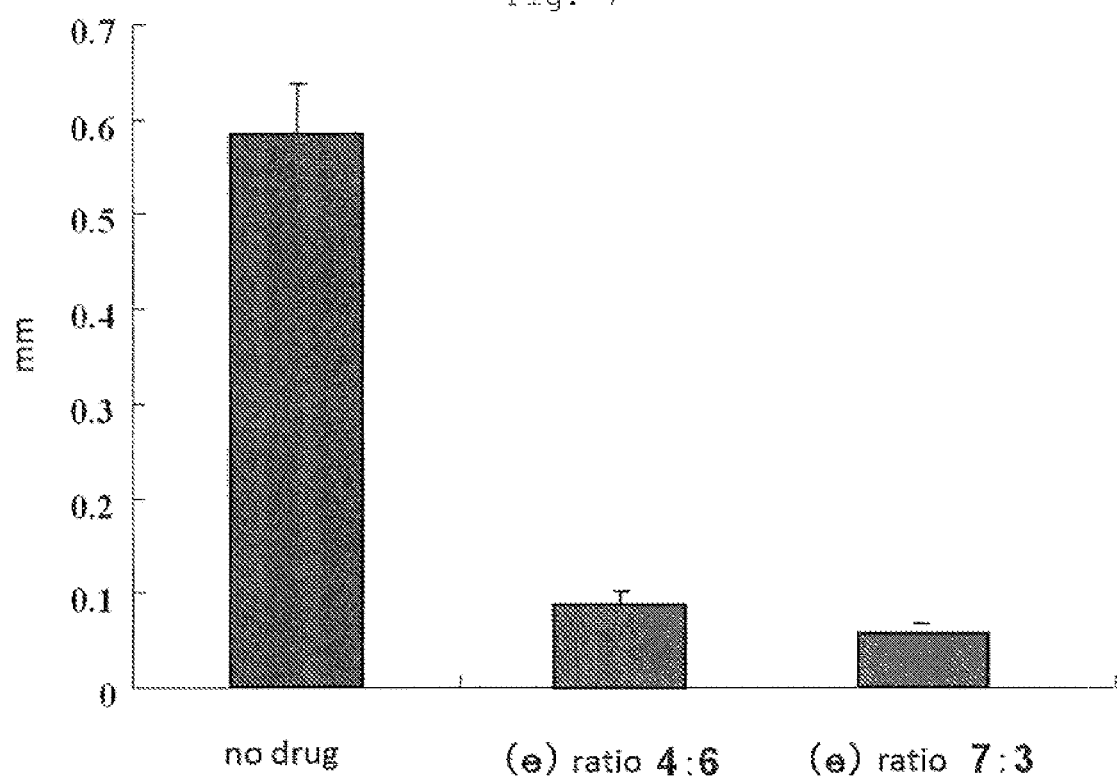
FIG. 7 shows the result of Example 4.

Stents were prepared with the above polymer (e), which were different at the mixture ratio of cilostazol (D) and the polymer (P) (D/P ratio). The prepared stents were placed in the iliac blood vessel of rabbits, and the effect of each stent to suppress intimal thickening was evaluated. The results are shown in FIG. 7.

The results show that both the stents having the mixture ratio (D/P ratio) of 4:6 or 7:3 could suppress intimal thickening more than the stent composed of only the base member (BMS) or the stent coated with only the polymer.

In addition, the observation of the endothelial cells at the stent-placing site showed that the endothelial cells could be well regenerated, and thus, the present stent coated with cilostazol was able to achieve the both effects of (1) suppressing intimal thickening and (2) suppressing the inhibitory of the vascular endothelial cell regeneration, which have not been achieved with limus-type drugs.

Example 5

Similarly, stents were prepared with the above polymer (e), wherein the mixture ratio of cilostazol and polymer (e) (D/P ratio) is fixed at 5:5, but the weight of cilostazol varied between 300 μg-600 μg. The prepared stents were placed in the iliac blood vessel of swine, and then (I) intima-media/vascular-media ratio, (II) neointimal area, and (III) vascular endothelial cell coverage, at the stent-placing site of the iliac blood vessel were evaluated 28 days after the placement.

Figure 8:
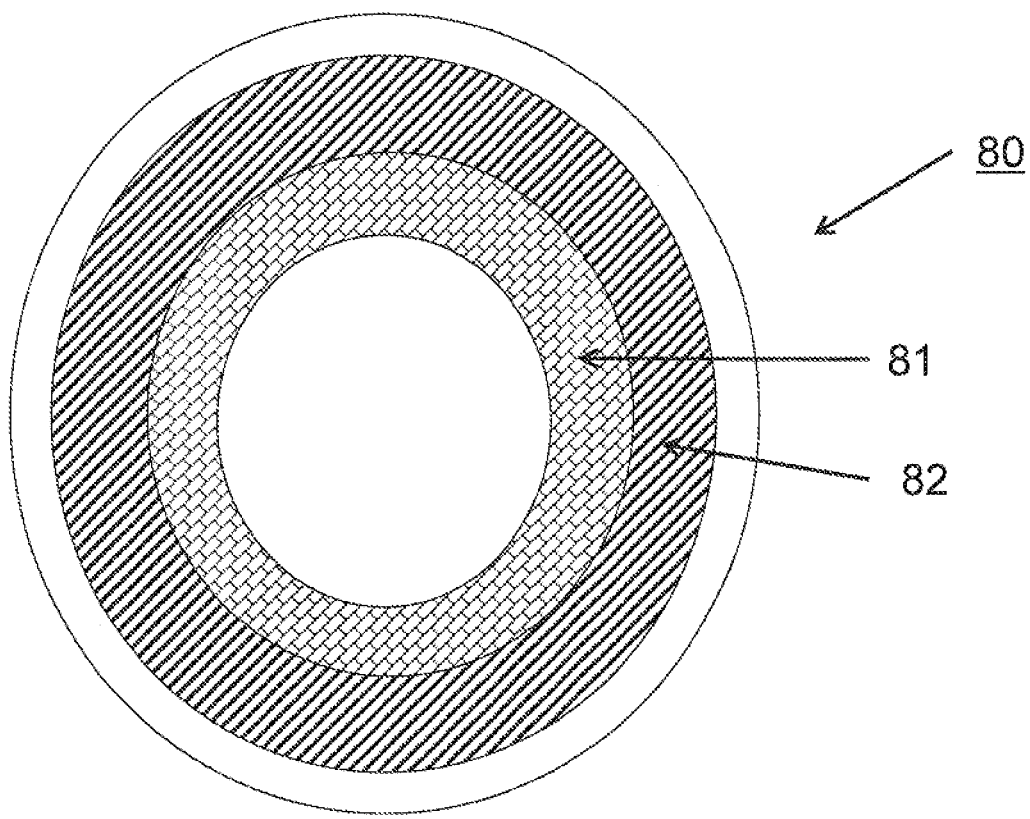
FIG. 8 shows a drawing for explaining Example 5.

The (II) neointimal area here denotes the cross-section area of intima-media 81 which is newly formed in the inside of blood vessel 80 at the stent-placing site, as shown in FIG. 8. The (I) intima-media/vascular-media ratio denotes the ratio of the above neointimal area to the cross-section area of vascular-media 82.

The evaluation was performed as follows:
(a) pulling out the iliac blood vessel,
(b) washing it, and then delipidating it,
(c) penetrating a resin, and then immobilizing it by polymerizing the resin,
(d) cutting it at the intended site, and
(e) staining it, and then observing it by microscopy.

Figure 9:
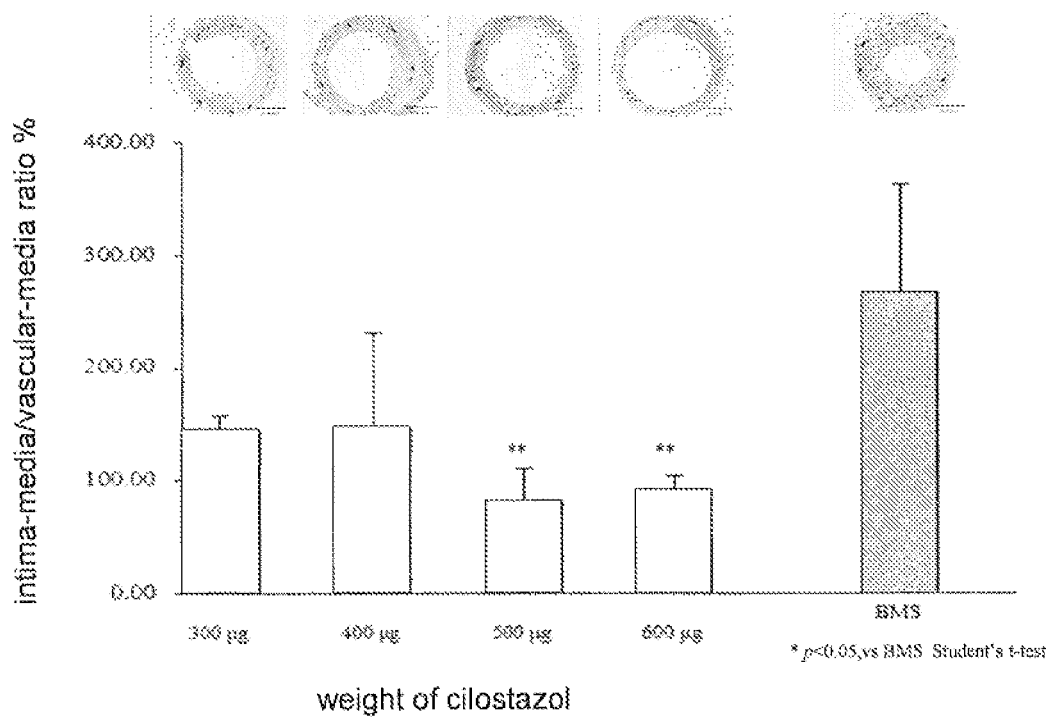
FIG. 9 shows the intima-media/vascular-media ratio which is the result of Example 5.

FIG. 9 shows each (I) intima-media/vascular-media ratio determined varying the weight of cilostazol. The upper of the figure shows pictures of each blood vessel cross-section which were taken 28 days after placing a stent loaded with each weight of cilostazol in the blood vessel. The data indicated by "BMS" herein is a result obtained by using a metal stent which is not coated with any drug or polymer.

According to FIG. 9, when the weight of cilostazol is more than 400 μg, the intima-media/vascular-media ratio falls to well below 100%, which indicates that the generation of the intima-media can be suppressed at the stent-placing site. In particular, when the weight of cilostazol is 500 μg or 600 μg, the intimal thickening can be significantly suppressed, compared with the case of the stent composed of only the base member (BMS) whose intima-media/vascular-media ratio is more than 260%.

However, when the weight of cilostazol is too much, the amount of the polymer needs to be increased. In such a case, the total amount of the coating agent should be swollen, and thereby it becomes difficult to form a strong and uniform coating. In addition, the result in FIG. 9 shows that the reduction of intima-media/vascular-media ratio has peaked when the weight of cilostazol is 500 μg-600 μg. Thus, the amount of cilostazol is preferably more than 400 μg and less than 700 μg, and in particular, more preferably more than 500 μg and less than 600 μg.

Figure 10:
FIG. 10 shows the neointimal area which is the result of Example 5.

FIG. 10 shows each (II) neointimal area determined varying the weight of cilostazol. FIG. 10 indicates that any cases of the stents coated with cilostazol can reduce the neointimal area, compared with the case of the stent composed of only the base member (BMS), and in particular, when the weight of cilostazol is more than 400 μg, the neointimal area is reduced a lot. In particular, when the weight of cilostazol is 600 μg, the neointimal area is significantly reduced, compared with the case of the stent composed of only the base member (BMS).

Figure 11:
FIG. 11 shows the endothelial coverage which is the result of Example 5.

FIG. 11 shows each (III) vascular endothelial cell coverage determined varying the weight of cilostazol. The result indicates that the coating with cilostazol and the polymer can make the vascular endothelial formulation easy at any weight of cilostazol, compared with the case of the stent composed of only the base member (BMS).

As shown at the results in FIG. 9-FIG. 11, the present invention can suppress intimal thickening at the stent-placing site, and prevent inhibiting the vascular endothelial cell regeneration. Thus, the amount of cilostazol is preferably more than 400 μg and less than 700 μg, and in particular, more preferably more than 500 μg and less than 600 μg.

EXPLANATIONS OF LETTERS OR NUMERALS

1: stent
2: base member
3: coating agent
4: ultrasonic spray coating machine
5: ultrasonic spray nozzle
6: pipe
80: cross-section of blood vessel
81: intima-media
82: vascular-media

The invention claimed is:

1. A drug-eluting stent having a net-like main body which is made of a metal or a polymeric material and has flection sections, wherein a surface of the main body is coated with a mixture comprising cilostazol and a bioabsorbable polymer, wherein the bioabsorbable polymer comprises
   (a) a polymer comprising DL lactide and glycolide in a weight ratio of 7:3-9:1, whose molecular weight is 40,000-400,000,
   (b) a polymer comprising DL lactide whose molecular weight is 50,000-100,000,
   (c) a polymer comprising L lactide and DL lactide in a weight ratio of 6:4-8:2, whose molecular weight is 300,000-600,000,
   (d) a polymer comprising L lactide whose molecular weight is 50,000-150,000, or
   (e) a polymer comprising L lactide and caprolactone in a weight ratio of 6:4-8:2, whose molecular weight is 150,000-400,000.

2. The drug-eluting stent as claimed in claim 1, wherein the bioabsorbable polymer comprises a polymer comprising DL lactide and glycolide in a weight ratio of 73:27-77:23, whose molecular weight is 63,000.

3. The drug-eluting stent as claimed in claim 1, wherein a weight ratio of cilostazol and the bioabsorbable polymer is 4:6-7:3.

4. The drug-eluting stent as claimed in claim 3 wherein the weight ratio of cilostazol and the bioabsorbable polymer is 4: 6-6:4.

5. The drug-eluting stent as claimed in claim 1, whose main body is made of a cobalt-chromium alloy as a main ingredient.

6. The drug-eluting stent as claimed in claim 1, wherein the mixture coated on the surface of the main body is coated by ultrasonic spraying.

7. The drug-eluting stent as claimed in claim 1, wherein the weight of the cilostazol applied on the stent is more than 400 μg and less than 700 μg.

8. The drug-eluting stent as claimed in claim 7, wherein the weight of the cilostazol applied on the stent is more than 500 μg and less than 600 μg.

* * * * *